(12) United States Patent
Wrobel

(10) Patent No.: US 8,272,269 B2
(45) Date of Patent: Sep. 25, 2012

(54) METHOD FOR EXAMINING A MEDIUM

(75) Inventor: Miroslaw Wrobel, Karlstadt (DE)

(73) Assignee: Wittenstein AG, Igersheim (DE)

(*) Notice: Subject to any disclaimer, the term of this patent is extended or adjusted under 35 U.S.C. 154(b) by 251 days.

(21) Appl. No.: 12/769,261

(22) Filed: Apr. 28, 2010

(65) Prior Publication Data

US 2010/0275690 A1 Nov. 4, 2010

(30) Foreign Application Priority Data

May 4, 2009 (DE) .......................... 10 2009 019 497

(51) Int. Cl.
*G01N 29/02* (2006.01)
*G01F 1/66* (2006.01)
*G06F 19/00* (2006.01)

(52) U.S. Cl. ............ 73/579; 73/602; 73/606; 73/861.18; 702/56

(58) Field of Classification Search .................... 73/579, 73/597, 602, 649, 657, 606, 861.18; 600/453, 600/455
See application file for complete search history.

(56) References Cited

U.S. PATENT DOCUMENTS

| | | | | |
|---|---|---|---|---|
| 3,665,716 A | * | 5/1972 | Rogers et al. ............ | 405/129.35 |
| 3,918,061 A | * | 11/1975 | Elgaard .......................... | 342/115 |
| 4,809,703 A | * | 3/1989 | Ishikawa et al. .............. | 600/454 |
| 5,343,285 A | * | 8/1994 | Gondrum et al. ............ | 356/28.5 |
| 5,872,536 A | * | 2/1999 | Lyons et al. ..................... | 342/70 |

FOREIGN PATENT DOCUMENTS

| | | |
|---|---|---|
| DE | 10036567 A1 | 2/2002 |
| DE | 10224294 A1 | 1/2004 |
| DE | 19944047 A1 | 4/2004 |
| DE | 699 37 747 T2 | 12/2008 |
| WO | WO02065152 * | 8/2002 |
| WO | 2005/009244 A1 | 2/2005 |
| WO | 2007/000047 A1 | 1/2007 |

* cited by examiner

*Primary Examiner* — J M Saint Surin
(74) *Attorney, Agent, or Firm* — Quarles & Brady LlP

(57) ABSTRACT

The present invention relates to a method for examining a medium (19), comprising the following steps of: transmitting a measurement input signal (4) comprising at least one measurement frequency, wherein the measurement input signal (4) is coupled into a medium (19); receiving a measurement output signal (9) emerging from the medium (9); transmitting a counter measurement input signal (13) comprising at least one counter measurement frequency, wherein the counter measurement frequency essentially corresponds to the measurement frequency, and wherein the counter measurement input signal (13) is coupled into the medium (19) simultaneously and in an opposite direction to the measurement input signal (4); receiving a counter measurement output signal (16) emerging from the medium (19); calculating a Doppler correction by comparing the counter measurement input signal (13) with the counter measurement output signal (16) in terms of the counter measurement frequency and by comparing the measurement input signal (4) with the measurement output signal (9) in terms of the measurement frequency; calculating a phase shift between the at least one measurement frequency of the measurement input signal (4) and the corresponding measurement frequency of the measurement output signal (9); correcting the phase shift as a function of the Doppler correction.

16 Claims, 4 Drawing Sheets

METHOD FOR EXAMINING A MEDIUM

CROSS REFERENCE TO RELATED APPLICATIONS

This application claims priority to German patent application no. 10 2009 019 497.5 filed 4 May 2009, which is incorporated herein by reference in its entirety for all purposes.

STATEMENT REGARDING FEDERALLY SPONSORED RESEARCH

Not applicable.

The present invention relates to a method for examining a medium.

From document WO 2007/000047 an ultrasonic interferometer is known which operates in line with the concept of simultaneous, multiple frequencies. Thereby, multiple-frequency ultrasonic waves pass through a medium to be classified and a phase shift is subsequently determined for each of said frequencies. Due to said group of phase shifts, the medium can be classified in various ways, since certain properties of specific mediums give rise to specific phase shifts for waves with specific frequencies passing through the medium. Besides, this device equally allows for determining the state of a process.

However, in the described device a phase shift which is caused by dynamical processes in the medium, such as motions, is not taken into account and said phase shift, which is also referred to as Doppler shift, distorts the phase shift to be determined which is desirable, for instance due to material constants.

In other words, using the known ultrasonic interferometer it is not possible to obtain the actual phase shift required for classifying the medium independently of a Doppler shift generated, as the case may be, by means of motions in the medium.

Hence, the known device involves the risk of misclassification due to the distortion of the phase shift required for the correct classification as a result of the Doppler shift.

Consequently, it is an object of the present invention to overcome the drawbacks cited above and to take into account a Doppler shift in determining a phase shift after passage through the medium.

This object is achieved by the present invention according to the teaching of the main claim.

Advantageous embodiments of the present invention are the subject-matter of the subclaims.

According to the invention, the problem is solved by the aspect that the method for examining a medium comprises the following steps of:

transmitting a measurement input signal comprising at least one measurement frequency, wherein the measurement input signal is coupled into a medium;

receiving a measurement output signal emerging from the medium;

transmitting a counter measurement input signal comprising at least one counter measurement frequency, wherein the counter measurement frequency essentially corresponds to the measurement frequency, and wherein the counter measurement input signal is coupled into the medium simultaneously and in an opposite direction to the measurement input signal;

receiving a counter measurement output signal emerging from the medium;

calculating a Doppler correction by comparing the counter measurement input signal with the counter measurement output signal in terms of the counter measurement frequency, and by comparing the measurement input signal with the measurement output signal in terms of the measurement frequency;

calculating a phase shift between the at least one measurement frequency of the measurement input signal and the corresponding measurement frequency of the measurement output signal;

correcting the phase shift as a function of the Doppler correction.

When examining a medium in terms of certain properties, for instance physical or chemical properties, constant measurement frequencies are frequently utilized, which are coupled into the medium to be examined in the form of a measurement input signal. Thereby, the number of measurement frequencies is basically inessential. To put it simply, an additional property can be determined by means of each additional measurement frequency and the examination is thusly simplified. In the following, at least one such measurement frequency is initially supposed to be present.

The measurement frequency in the measurement input signal is basically freely selectable, but may for instance be contingent upon the property to be determined. During a measurement cycle, however, the measurement frequency, in particular, remains constant but may be altered specific to each individual measurement cycle.

The measurement input signal is then coupled into the medium to be examined. Subsequently, the coupled measurement input signal passes through the medium and emerges from the medium, for instance at an opposite site, in the form of a measurement output signal. At this site, the measurement output signal emerging from the medium is captured and received.

Simultaneously with transmitting and coupling of the measurement input signal, a counter measurement input signal is transmitted. Said counter measurement input signal is required to comprise the measurement frequency of the measurement input signal, substantially in the form of a counter measurement frequency. Said counter measurement frequency is preferably selected so as to be invariable. In the event that several measurement frequencies are present in the measurement input signal, the counter measurement input signal is required to comprise at least one of said measurement frequencies in the form of a counter measurement frequency. Due to the essentially identical frequency in the counter measurement input signal and in the measurement input signal, it is possible to ensure that both signals are subject to a comparable Doppler shift.

Moreover, the counter measurement input signal is coupled into the medium in an opposite direction to the measurement input signal. As a result of this measure, two comparable frequencies, i.e. the measurement frequency and the counter measurement frequency, pass through the medium to be examined in opposite directions. Direction-dependent properties of the medium to be examined can be determined by using said, strictly speaking two, measurement cycles.

The counter measurement input signal coupled into the medium passes through the medium to be examined and emerges from the medium in the form of a counter measurement output signal, for instance on the opposite side. On this side, the counter measurement input signal can be captured and received in the form of a counter measurement output signal.

As a result, in fact four signals are present, i.e. the counter measurement input signal, the counter measurement output signal, the measurement input signal and the measurement output signal. However, it should be noted that the measurement input signal and the counter measurement input signal may resemble each other, insofar as both signals comprise only one frequency in the form of a measurement frequency or counter measurement frequency.

For determining the properties of interest, the determination of the phase shift between the at least one measurement frequency of the measurement input signal and the corresponding measurement frequency of the measurement output signal is performed as already known from the state of the art. Thereby, phase-dependent properties can be determined and the medium can be classified.

Said phase shift calculated in terms of the measurement frequency, when regarded in isolation, contains two phase shift components, i.e. at least one material constant-dependent component and one flow-dependent component. The material constant-dependent component is thereby for instance created as a result of density variations in the medium and the flow-dependent component is for instance created as a result of a Doppler shift due to a flow velocity. In the methods used hitherto, said components were inseparable and the flow-dependent component or Doppler component distorted the material constant-dependent component which is actually the only one of interest.

For this reason, in the method according to the present invention a Doppler correction is calculated by comparing the counter measurement input signal with the counter measurement output signal in terms of the counter measurement frequency, and by comparing the measurement input signal with the measurement output signal in terms of the measurement frequency. Subsequently, the phase shift is corrected as a function of the Doppler correction. As a result, only the material constant-dependent component of the phase shift is obtained, which is the only one of interest.

The effects attained by said approach are enhanced by the aspect that the Doppler-dependent component of the phase shift in the medium is direction-dependent, since the parameter underlying the same, i.e. velocity, is a directed parameter, and the aspect that the material constant-dependent component of the phase shift in the medium is not direction-dependent. By means of this aspect, the Doppler-dependent component of the phase shift can be separately determined by performing a determination from various directions, and the Doppler-dependent component of the phase shift can then be identified to constitute a Doppler-dependent phase shift or else can be converted into a velocity value of the flow which causes the Doppler shift and can be further processed.

As a result, for the actual determination of the property of interest or of the properties of interest of the medium, a more definite phase shift is obtained, on the basis of which the phase shift-dependent parameter of interest can be obtained, since said phase shift no longer contains the flow-dependent component or Doppler-dependent component. As a consequence, a classification of the medium which is performed on the basis of the measurement results is rendered more accurate. By averaging the measurement values and capturing a plurality of measurement values, variances are minimized and a measurement value obtained is rendered more accurate. The risk of misclassifications is thusly reduced.

In addition, said method provides the advantage that, if the measurement input signal comprises several measurement frequencies for simultaneously determining several properties of the medium to be examined, the Doppler correction needs to be performed only one time with the aid of one measurement frequency from the measurement frequencies contained in the measurement input signal, since in the Doppler correction obtained, the velocity of the flow which causes the Doppler shift is contained. On the basis of said velocity obtained, all of the phase shifts obtained from the measurement due to the multiple measurement frequencies contained in the measurement input signal can be corrected.

The type of the signal is basically optional. According to a preferred embodiment, the signals are generated in the form of ultrasonic waves and according to another preferred embodiment, the signals are generated in the form of electromagnetic waves. However, it is also possible to utilize both types of waves in combination.

In order to achieve a good response characteristic of an ultrasonic transmitter when utilizing ultrasonic waves, according to another preferred embodiment the ultrasonic waves obey a mathematically smooth function.

According to another preferred embodiment, transmission of the counter measurement input signal and transmission of the measurement input signal are performed in a simultaneous and continuous fashion with the aid of different transmitters. By means of this aspect, the transmitters can be dimensioned specific to the respective application, for instance as a narrow band or as a broad band transmitter, and no dead times occur in determining the flow-dependent Doppler shift. In dynamical processes, this aspect provides special advantages, since both for the calculation of the phase shift and for the calculation of the Doppler correction measurement data are available in a continuous fashion and at any time.

According to another preferred embodiment, transmission and reception of the counter measurement input signal, the counter measurement output signal, the measurement input signal and the measurement output signal are performed with the aid of a switchable transmitter/receiver unit. By respectively arranging a combined transceiver on each opposite side, the counter measurement input signal and the measurement input signal can be transmitted simultaneously in opposite directions and can be coupled into the medium if both transceivers are in the transmission mode. After a suitable time, the two transceivers are switched into the reception mode and can receive the signal transmitted by the respectively opposite transceiver which has been configured as a transmitter beforehand. In this way, the number of components required for a device for performing said method can be reduced and the device is consequently rendered more compact.

In the further course of said method variation, subsequent to reception of the signals a switch-back into the transmission mode is performed and the cycle is started again.

According to another preferred embodiment, the transmitter/receiver unit is switched at the latest when one of the signals has reached the opposite reception site. Thereby, one the one hand it is possible to ensure that the entire distance between the two transceivers is used for the measurement, and on the other hand it can be ensured that the switching intervals are kept as short as possible in order to thusly keep the total time required for the measurement as short as possible.

According to another preferred embodiment, the signals in the medium follow a substantially common or at least adjacent trajectory. By means of this aspect, it can be achieved that both the signal coupled in the form of a measurement input signal and the signal coupled in the form of a counter measurement input signal cover approximately the same distance in the medium. Thus, in the best-case scenario, both signals experience the same variations, in particular flows.

In principle, proximity of the signal trajectories would suffice for achieving said effect. In case of a perfectly identical trajectory, maximum optimization may for instance be realized by transmission with the aid of a switchable transmitter/receiver unit.

According to another advantageous embodiment, the method is utilized for detecting a density variation, especially in the event of a stroke. Strokes may on the one hand for instance be caused by an obstructed blood vessel in the head region or else by a burst blood vessel in the head region. When a blood vessel in the head region bursts, for instance the discharged blood is consequently mixed with cerebrospinal fluid. Both instances give rise to density variations, which can be detected in a phase-dependent fashion using the inventive method.

According to another advantageous embodiment, the inventive method is used for classifying the medium with the Doppler effect eliminated.

According to another advantageous embodiment, the inventive method is used for determining physical motions in the medium. Hence, for instance the reactivity of the medium, especially flow conditions, can be determined on the basis of the obtained Doppler correction or Doppler velocity.

In the event of a stroke, a carotid branch is frequently obstructed and blocked, which aspect in a measurement in the plane of the carotids according to the present invention will give rise to a resultant velocity of ≠0, and thusly a Doppler correction of ≠0 will be obtained, since in a healthy human, the two partial velocities of the right and left carotid branches in the plane would in fact sum up to form 0 in a reverse manner and would ultimately result in a Doppler correction of approximately 0.

According to another advantageous embodiment, the inventive method is used for determining the flow rate.

According to another advantageous embodiment, the inventive method is used for characterizing the dispersivity of the medium.

According to another advantageous embodiment, the inventive method is used for tomographical imaging of the medium to be examined.

According to another advantageous embodiment, the inventive method is used for tomographical 3D helix imaging of the medium to be examined.

Various embodiments are illustrated in the drawings and will be exemplarily specified in the following and are not restrictive of the scope of the present invention.

In the drawings:

FIG. 1 illustrates a first embodiment of the inventive method performed on the basis of transmission of counter signal and measurement signal in a simultaneous and continuous fashion and in opposite directions.

Figure 1:
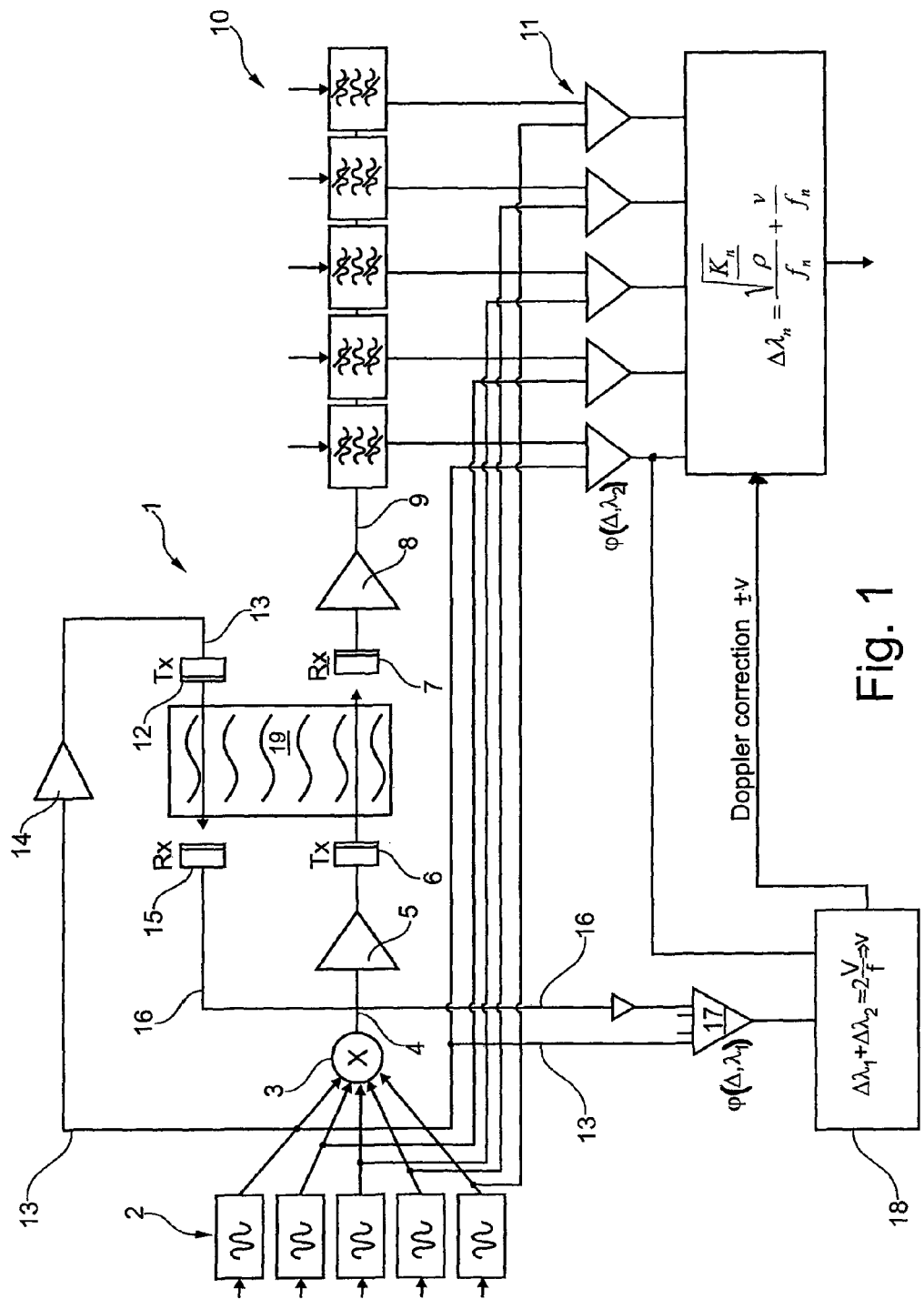
FIG. 1 illustrates a first embodiment of the inventive method performed on the basis of a transmission of counter signal and measurement signal in a simultaneous and continuous fashion and in opposite directions.

A device 1 for performing the method comprises individual signal generators 2 each generating a signal with a constant frequency. Said signals are mixed using a mixing element 3 to form a measurement input signal 4 and are amplified using the amplifier 5 in order to be subsequently conveyed to the transmitter 6.

Hence, the measurement input signal 4 conveyed by the transmitter 6 contains several constant measurement frequencies for simultaneous examination of the medium 19 in terms of different properties. Thus, for instance in case of different phase shifts at different frequencies, a classification can be performed with the aid of said profile.

Using the transmitter 6, the measurement input signal 4 is coupled into the medium 19, passes through the medium 19 and is received by the receiver 7 on the opposite side in the form of a measurement output signal 9. Subsequently, the measurement output signal 9 is conveyed to filter elements 10 and is filtered therein in terms of the frequencies preset by the individual signal generators 2.

The signals split up in terms of the individual frequencies are conveyed to calculation elements 11 and are compared with the respectively corresponding frequency in the measurement input signal preset by the individual signal generator 2. Consequently, a phase shift is obtained for each measurement frequency.

The phase shifts are respectively subject both to the impact of the properties to be examined of the medium 19 and to a Doppler shift which is caused in the medium 19 as a result of flows. Due to the fact that the Doppler shift is also identified as constituting a phase shift, the same distorts the phase shifts of interest which are caused by the properties of interest, such as density, viscosity and/or elasticity. As a result, the phase shifts obtained by the calculation element 11 contain two components, i.e. the component which is created by the property to be examined and the component which is created by the flows in the medium 19.

Hence, as a result, a combination of both components is initially calculated by the calculation elements 11 in total. Without any further correction, said distorted values for instance give rise to misclassification.

For this reason, the device 1 further comprises a transmitter 12 for transmitting a counter measurement input signal 13. The counter measurement input signal 13 contains an individual signal with constant counter measurement frequency generated by an individual signal generator 2 subsequent to amplification using the amplifier 14. Said individual signal has already been mixed into the measurement input signal 4 already in the form of a measurement frequency using the mixing element 3.

After coupling the counter measurement input signal 13 into the medium 19 with the aid of the transmitter 12, the counter measurement input signal 13 passes through the medium 19 in order to be received by the receiver 15 in the form of a counter measurement output signal 16 on the opposite side. The transmission paths between transmitter 12 and receiver 15 as well as between transmitter 6 and receiver 7 are thereby arranged adjacently in such a manner that the signals passing through said paths in the medium follow a substantially common or at least adjacent trajectory. Hence, both signals, i.e. the counter signal and the measurement signal, and hence likewise the counter measurement frequency and the measurement frequency, are exposed to nearly the same impacts.

Moreover, the transmitters 6 and 12 and receivers 7 and 15 are arranged in such a manner that the measurement signal and the counter signal pass through the medium 19 in opposite directions to calculate the Doppler velocity, which is a directed parameter, from different directions and to be thusly capable of determining the same.

Moreover, by means of the separately provided transmission paths between transmitter 6 and receiver 7 for the measurement signal and between transmitter 12 and receiver 15 for the counter signal, a continuous transmission of both signals can be ensured and thusly no dead times occur in the measurement.

Said simultaneous and continuous transmission provides special advantages especially in dynamical processes.

The counter measurement input signal 13 and the counter measurement output signal 16 are conveyed to a calculation element 17 and are compared there in terms of the counter measurement frequency. The calculation element 17 calculates a phase shift $\Delta\lambda_1$ experienced by the counter measurement frequency when passing through the medium 19.

The phase shift $\Delta\lambda_2$ obtained from the comparison of the measurement input signal 4 with the measurement output signal 9 in terms of the measurement frequency essentially corresponding to the counter measurement frequency and the phase shift $\Delta\lambda_1$ obtained from the comparison of the counter measurement input signal 13 with the counter measurement output signal 16 in terms of the counter measurement frequency are conveyed to a calculation element 18. Via a compression module, both phase shifts $\Delta\lambda_1$ and $\Delta\lambda_2$ contain a phase shift $$\Delta\lambda_c = \sqrt{\frac{K_c}{\rho}} \big/ f$$

which is contingent upon the density of the medium 19 and a phase shift (i.e. Doppler shift)

$$\Delta\lambda_V = \frac{v}{f}$$

which is contingent upon the flow velocity in the medium 19. Hence, the function $\Delta_i = \Delta_c \pm \Delta\lambda_v$ applies.

In the Doppler measurement, only the velocity component in the measurement plane is detectable. Said velocity component is directed either towards the side of the transmitter 6 and the receiver 15 or else towards the side of the receiver 7 and the transmitter 12, unless the same is equal to 0. Hence, the Doppler shift is incorporated into the two phase shifts $\Delta\lambda_1$ and $\Delta\lambda_2$ with an opposite sign and the following function applies (or vice versa):

$$\Delta\lambda_1 = \Delta\lambda_c + \Delta\pi_v \text{ and } \Delta\lambda_2 = \Delta\lambda_c - \Delta\lambda_v$$

In the calculation element 18, the two phase shifts $\Delta\lambda_1$ and $\Delta\lambda_2$ are then summed up one time and are subtracted from one another one time in an equation system so that after formation of the Doppler shift v the following function applies:

$$v = \frac{f(\Delta\lambda_1 - \Delta\lambda_2)}{2}$$

Thus, the Doppler velocity has been determined by means of two Doppler measurements performed in opposite directions in the calculation element 18, and on the one hand can be utilized as a physical parameter for determining the reactivity of the medium 19, or on the other hand can be utilized for correcting all phase shifts obtained from the calculation elements 11.

Even though the Doppler measurement has been performed only by utilizing a selected measurement frequency, it is nevertheless possible to correct all phase shifts which correspond likewise to other measurement frequencies from the calculation elements 11 using the Doppler effect, since to this end, knowledge of the Doppler velocity v is sufficient.

Figure 2:
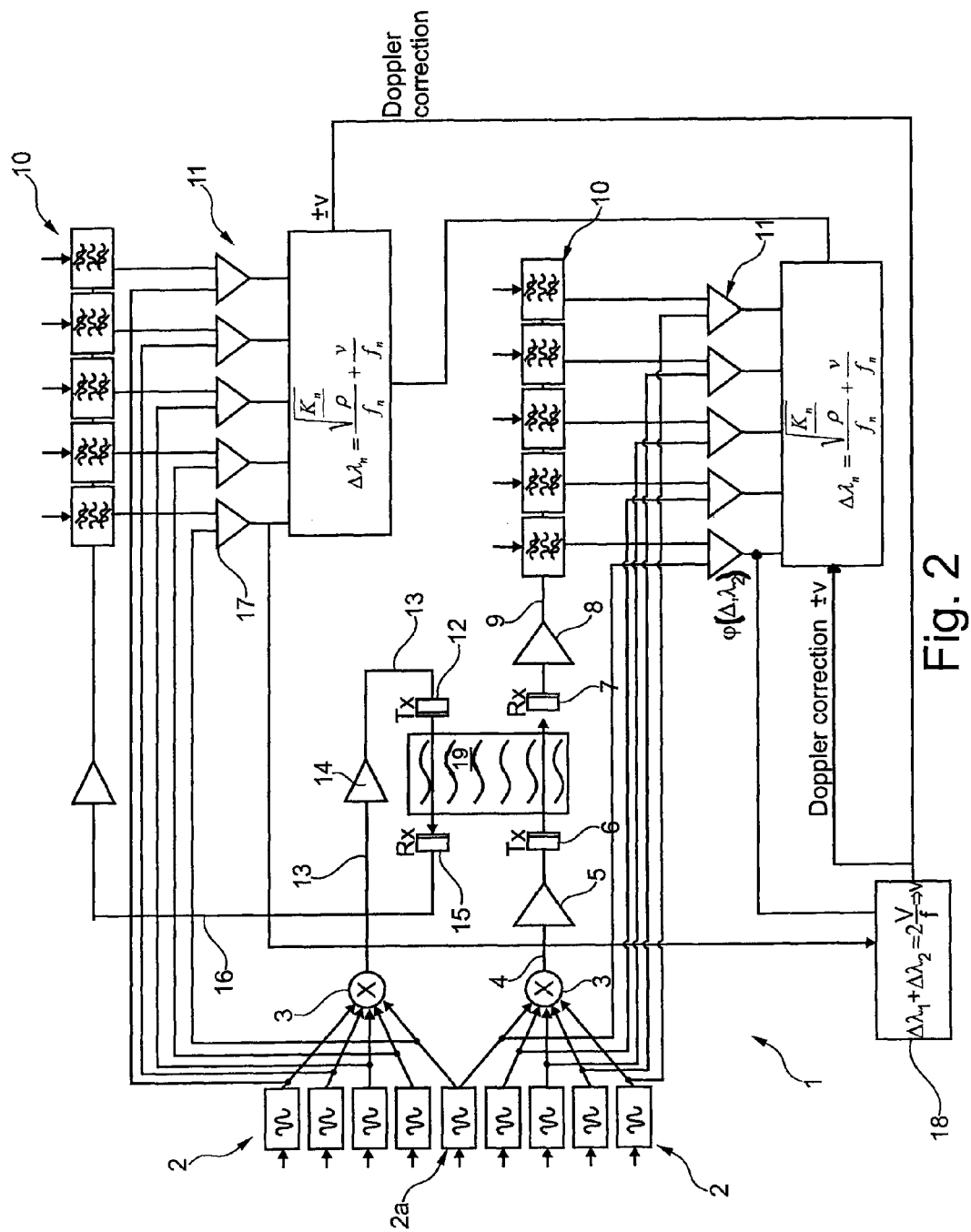
FIG. 2 illustrates a second embodiment of the inventive method performed on the basis of a transmission of counter signal and measurement signal in a simultaneous and continuous fashion and in opposite directions.

FIG. 2 illustrates a second embodiment, wherein the individual signals generated by the individual signal generators 2 are allocated to the transmission paths between transmitter 6 and receiver 7 and between transmitter 12 and receiver 15 in an essentially uniform fashion, and are then accordingly captured and conveyed to the further filter elements 10. This measure allows for achieving enhanced system efficiency.

Respectively four of the individual signals generated by the individual signal generators 2 are mixed with respectively one mixing element 3 to form the measurement input signal 4 and to form the counter measurement input signal 13. Thereby, both signals 4, 13, i.e. the measurement input signal 4 in the form of a measurement frequency and the counter measurement input signal 13 in the form of a counter measurement frequency, are each additionally mixed with a fifth individual signal. Due to the aspect that the measurement frequency and the counter measurement frequency emanate from the same individual signal generator 2a, they are essentially identical.

In contrast to the first embodiment according to FIG. 1, the received counter measurement output signal 16 is firstly conveyed to the filter elements 10. The partial signal filtered in terms of the counter measurement frequency (as in the case of the first embodiment) is then conveyed to one calculation element 17 of the calculation elements 11, and the resultant phase shift $\Delta\lambda_1$ (as in the case of the first embodiment) is conveyed to the calculation element 18 which then calculates the Doppler correction.

Figure 3:
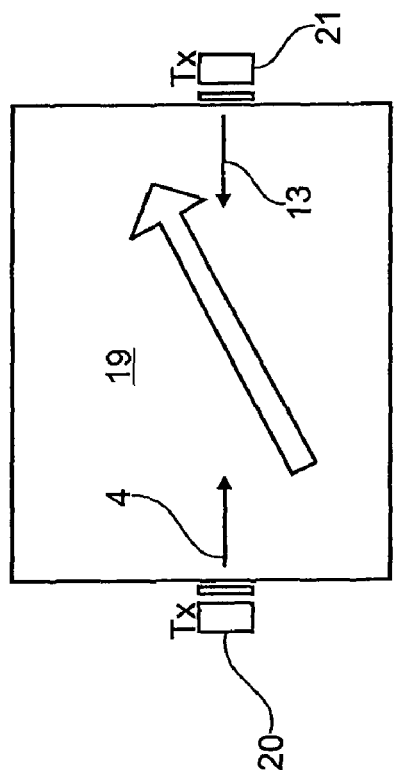
FIG. 3 illustrates a third embodiment of the inventive method performed with the aid of a switchable transmitter/receiver unit when the same functions as a transmitter.

FIG. 3 illustrates an embodiment of the inventive method using a switchable transmitter/receiver unit. The transmitter/receiver unit in this embodiment is in the transmission mode and both the first transceiver 20 and the second transceiver 21 are switched as transmitters. The transceiver 20 transmits the measurement input signal 4 and couples the same into the medium 19. The transceiver 21 transmits the counter measurement signal 13 and couples the same into the medium 19. Both signals then pass through the medium 19 in opposite directions and travel therein.

Figure 4:
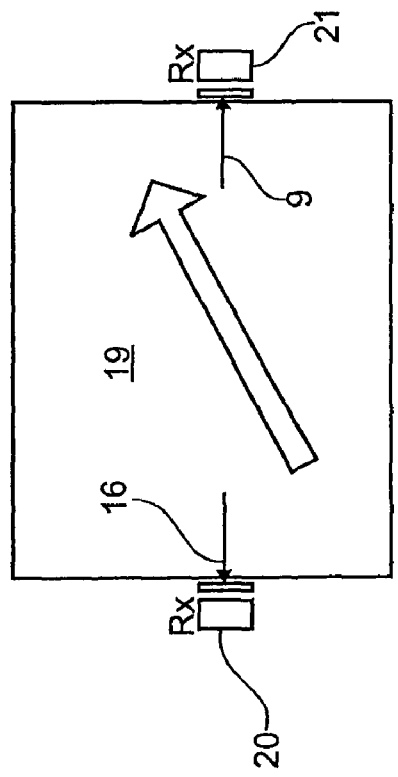
FIG. 4 illustrates a fourth embodiment of the inventive method performed with the aid of a switchable transmitter/receiver unit when the same functions as a receiver.

FIG. 4 illustrates the embodiment of FIG. 2 at a later stage. The transceivers 20 and 21 are switched as receivers. In the meantime, the signals have traveled and the counter measurement output signal 16 is received by the transceiver 20. The measurement output signal 9 is received by the transceiver 21. The switching time of the transceivers 20, 21 into the reception mode has thereby been selected in such a manner that the switching is performed when the signals have respectively reached the opposite transceiver.

Figure 5:
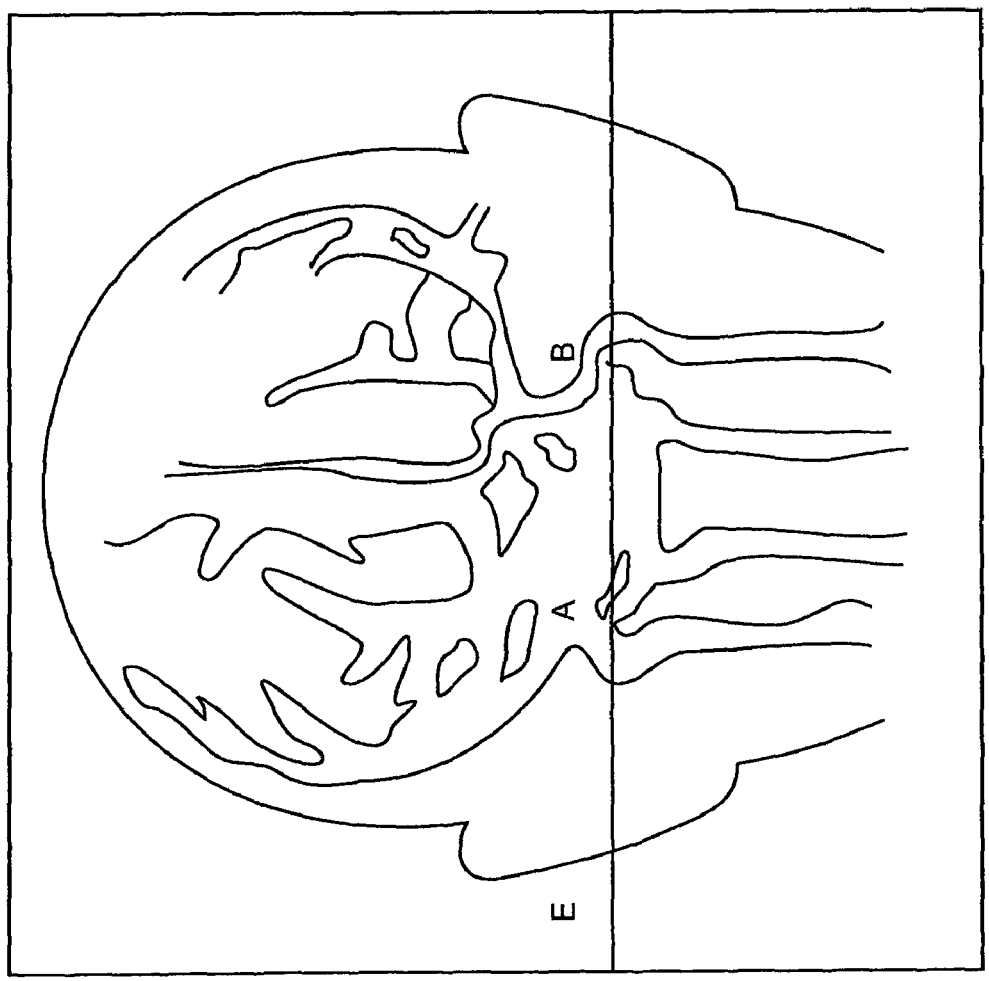
FIG. 5 illustrates the use of the inventive method in the detection of a stroke.

FIG. 5 illustrates the option of detecting a stroke using the inventive method.

Thereby, the measurement is performed in plane E in which the two carotidal regions A and B are located.

In a healthy patient, the velocity component in region A and the velocity component in region B are directed in opposite directions and sum up to form 0.

In the event of a stroke, the blood flow in one of said regions is frequently inhibited or caused to collapse due to an obstructed or narrowed blood vessel. In this instance, the velocities of the two regions do not sum up to form 0 and a resultant Doppler velocity is detectable using the above described method.

In other words, it can be inferred from a Doppler velocity $v \neq 0$ obtained using the above described method that a reduced blood flow is supposed to prevail in one of regions A or B, as compared to the respectively other region, which aspect is indicative of an obstructed blood vessel and consequently of a stroke.

The invention claimed is:

1. A method for examining a medium, comprising the following steps of:
   transmitting a measurement input signal comprising at least one measurement frequency, wherein the measurement input signal is coupled into a medium;
   receiving a measurement output signal emerging from the medium;
   transmitting a counter measurement input signal comprising at least one counter measurement frequency, wherein the counter measurement frequency essentially corresponds to the measurement frequency, and wherein the counter measurement input signal is coupled into the medium simultaneously and in an opposite direction to the measurement input signal;
   receiving a counter measurement output signal emerging from the medium;
   calculating a Doppler correction by comparing the counter measurement input signal with the counter measurement output signal in terms of the counter measurement frequency, and by comparing the measurement input signal with the measurement output signal in terms of the measurement frequency;
   calculating a phase shift between the at least one measurement frequency of the measurement input signal and the corresponding measurement frequency of the measurement output signal; and
   correcting the phase shift as a function of the Doppler correction.

2. A method according to claim 1, in which the signals are generated in the form of ultrasonic waves.

3. A method according to claim 2, in which the ultrasonic waves obey a mathematically smooth function.

4. A method according to claim 1, in which the signals are generated in the form of electromagnetic waves.

5. A method according to claim 1, in which the signals are generated both in the form of ultrasonic waves and in the form of electromagnetic waves.

6. A method according to claim 1, in which transmission of the counter measurement input signal and transmission of the measurement input signal are performed in a simultaneous and continuous fashion with the aid of different transmitters.

7. A method according to claim 1, in which transmission and reception of the counter measurement input signal, the counter measurement output signal, the measurement input signal and the measurement output signal are performed with the aid of a switchable transmitter/receiver unit.

8. A method according to claim 7, in which the transmitter/receiver unit is switched at the latest when one of the signals has reached the opposite reception site.

9. A method according to claim 1, in which in the medium, the signals follow a substantially common or at least adjacent trajectory.

10. The method according to claim 1 in which a density variation of the medium is detected, in particular in event of a stroke.

11. The method according to claim 1 in which the medium is classified with the Doppler effect eliminated.

12. The method according to claim 1 in which physical motions in the medium are determined.

13. The method according to claim 1 in which a flow rate of the medium is determined.

14. The method according to claim 1 in which dispersivity of the medium is characterized.

15. The method according to claim 1 including generating a tomographical image of the medium to be examined.

16. The method according to claim 1 including generating a tomographical 3D helix image of the medium to be examined.

* * * * *

UNITED STATES PATENT AND TRADEMARK OFFICE
CERTIFICATE OF CORRECTION

PATENT NO. : 8,272,269 B2
APPLICATION NO. : 12/769261
DATED : September 25, 2012
INVENTOR(S) : Miroslaw Wrobel It is certified that error appears in the above-identified patent and that said Letters Patent is hereby corrected as shown below:

In the Specifications:

Column 7, line 40, "$\Delta_i=\Delta_c\pm\Delta\lambda_v$" should be -- $\Delta\lambda_i=\Delta\lambda_c\pm\Delta\lambda_v$ --.

Column 7, line 50, "$\Delta\lambda_1=\Delta\lambda_c+\Delta\pi_v$" should be -- $\Delta\lambda_1=\Delta\lambda_c+\Delta\lambda_v$ --.

Signed and Sealed this
Twentieth Day of November, 2012

David J. Kappos
*Director of the United States Patent and Trademark Office*